US00PP08001P

United States Patent [19]

McGredy, IV

[11] Patent Number: Plant 8,001

[45] Date of Patent: Oct. 13, 1992

[54] HYBRID TEA ROSE NAMED 'HOAGY CARMICHAEL'

[75] Inventor: Sam McGredy, IV, Auckland, New Zealand

[73] Assignee: Roses by Fred Edmunds, Inc., Wilsonville, Oreg.

[21] Appl. No.: 643,927

[22] Filed: Jan. 18, 1991

[51] Int. Cl.[5] ..... A01H 5/00

[52] U.S. Cl. ..... Plt./21

[58] Field of Search ..... Plt./20, 21

[56] References Cited

U.S. PATENT DOCUMENTS

P.P. 5,519 7/1985 McGredy, IV ..... Plt. 20

*Primary Examiner*—Howard J. Locker

*Attorney, Agent, or Firm*—Christie, Parker & Hale

[57] ABSTRACT

A new hydrid tea rose with bright red flowers.

1 Drawing Sheet

SUMMARY OF THE INVENTION

The present invention relates to a new and distinct variety of rose plant of the hybrid tea rose class which was originated by my crossing as seed parent an unnamed and unpatented seedling of my creation and as pollen parent the variety known as 'Karma'. The varietal denomination of this new rose is 'Hoagy Carmichael.'

Among the novel characteristics possessed by this new variety which distinguishes it from its parents and all other varieties of which I am aware are its attractive well formed bright red flowers borne on a plant particularly suitable for growing outdoors in gardens. Flowers open well and hold their coloring as blooms age. Asexual reproduction by propagation by budding of the new variety as performed in Clackamas County, Oreg., shows that the foregoing and other distinguishing characteristics come true to form and are established and transmitted through succeeding propagations.

BRIEF DESCRIPTION OF ILLUSTRATION

The accompanying illustration shows typical specimens of the vegetative growth and flowers of the new variety in different stages of development and depicted in color as nearly true as it is reasonably possible to make the same in a color illustration of this character.

DESCRIPTION OF THE NEW VARIETY

The new variety is an unusually fine hybrid tea rose with a rich, clear, substantially unfading color to petal drop, even in extreme heat. Flowers are perfectly spiraled, well shaped and of good exhibition-type form. Petals roll and quill to points, giving a star-like appearance to the blooms.

The following is a detailed description of my new variety, with color terminology in accordance with The Royal Horticultural Society Colour Chart (R.H.S.C.C.). The terminology used in color description herein refers to plate numbers in the aforementioned color chart.

Parentage: Seedling.

*Seed parent.*—Unnamed seedling.

*Pollen parent.*—'Karma'.

Class: Hybrid tea.

The following information is from observations made of specimens grown outdoors in Clackamas County, Oreg.

FLOWER

Blooming habit: Continuous.

A. Bud:

(1) *Size.*—Large.

(2) *Form.*—Long pointed.

(3) *Color.*—As sepals divide, bud color is near 46A.

(4) *Sepals.*—Longer than bud, simple to foliated, glabrous outside, inside wooly.

(5) *Penduncle.*—Length: Medium. Aspect: Straight. Strength: Erect. Color: Near 138B.

B. Bloom:

(1) *Size.*—Average size when fully expanded — about 5½ inches.

(2) *Borne.*—Singly, one to a stem, side buds rare.

(3) *Form.*—High centered at first, quilling of petals is distinctive, center holds until petals fall, stamens rarely show.

(4) *Petalage.*—Number of petals under normal conditions — about 40 to 45.

(5) *Color.*—After sepals fall and petals unfurl, predominant flower color viewing petals' top surface is near 45B; petals' undersurface is near 46A to 45B. Color is general and substantially constant. General tonality from a distance is near 45A. Color of petal point of attachment is near 11C. As blooms age, coloration approaches near 46C.

C. Petals:

(1) *Texture.*—Thick, pronounced substance.

(2) *Appearance.*—Inside velvety and outside satiny.

(3) *Form.*—Broad, fan shaped with some indentation or undulation at margin.

(4) *Arrangement.*—Regularly arranged, imbricated.

(5) *Petaloids in center.*—Few, large.

(6) *Persistence.*—Petals drop off cleanly.

(7) *Fragrance.*—Slight, sweet.

(8) *Lasting quality.*—Long lasting on plant, slow opening.

REPRODUCTION ORGANS

A. Stamens, filaments and anthers:

*Arrangement.*—Few regularly arranged, uneven.

*Color.*—Filaments near 55A, anthers near 21B.

B. Pollen:
*Color.*—Near 26B.
C. Styles: Many, densely packed, short, even, near 66A.
D. Stigmas:
*Color.*—Shaft near 66A, stigmatic surface near 18B.
E. Hips: None observed.

PLANT

A. Form: Upright.
B. Growth: Vigorous, height attained about 4 to 5 ft.
C. Foliage: Compound, generally 5 leaflets.
(1) *Size.*—Medium.
(2) *Quantity.*—Abundant, close set.
(3) *Color.*—New foliage: Upper side — near 59B. Under side — near 58A. Old foliage: Upper side — near 136B. Under side — near 138C.
(4) *Shape.*—Ovate, mucronate.
(5) *Texture.*—Upper side is glossy; under side is matte.
(6) *Edge.*—Serrate.
(7) *Serration.*—Ordinary.
(8) *Leaf stem.*—Color — near 144B; underside near 153B.
(9) *Stipules.*—Medium length, lightly bearded.
(10) *Resistance to disease.*—Mildew — Average. Blackspot — Average. Rust — Average.
D. Wood:
(1) *New wood.*—Color — near 144B. Bark — smooth.
(2) *Old wood.*—Color — near 144A. Bark — smooth.
E. Thorns:
(1) *Thorns.*—Quantity (main stalk) — Ordinary. Form — decurrent base, recurved Length — long. Color — near 34D. Position — regular.
(2) *Prickles.*—Few on main stalks, none on laterals.
F. Winter hardiness: Needs protection in severe climates.

I claim:

1. A new distinct variety of rose plant of the hybrid tea rose class, substantially as shown and described.

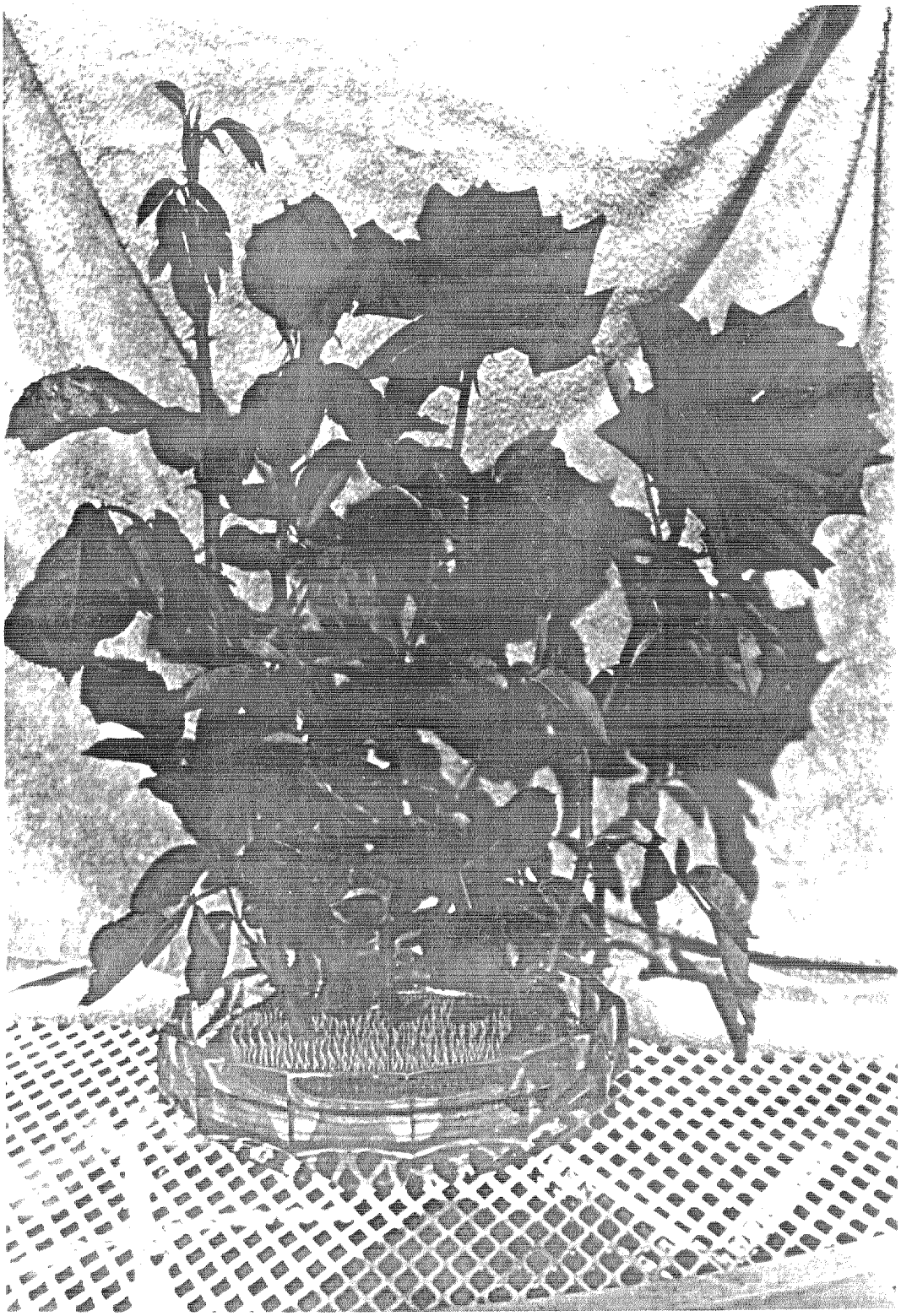

* * * * *